United States Patent [19]

Blake

[11] 4,446,581

[45] May 8, 1984

[54] INTRAOCULAR LENS WITH FREE-ENDED SIZING PRONG

[76] Inventor: Larry W. Blake, 2885 Regis La., Costa Mesa, Calif. 92626

[21] Appl. No.: 295,464

[22] Filed: Sep. 2, 1981
(Under 37 CFR 1.47)

[51] Int. Cl.³ .............................. A61F 1/16; A61F 1/24
[52] U.S. Cl. ............................................................. 3/13
[58] Field of Search ........................................... 3/13, 1

[56] References Cited

U.S. PATENT DOCUMENTS

| | | | |
|---|---|---|---|
| 2,834,023 | 5/1958 | Lieb | 3/13 X |
| 3,925,825 | 12/1975 | Richards et al. | 3/13 |
| 3,975,779 | 8/1976 | Richards et al. | 3/13 |
| 4,014,049 | 3/1977 | Richards et al. | 3/13 |
| 4,092,743 | 6/1978 | Kelman | 3/13 |
| 4,110,848 | 9/1978 | Jensen | 3/13 |
| 4,159,546 | 7/1979 | Shearing | 3/13 |
| 4,174,543 | 11/1979 | Kelman | 3/13 |
| 4,203,168 | 5/1980 | Rainin et al. | 3/13 |
| 4,215,440 | 8/1980 | Worst | 3/13 |
| 4,242,760 | 1/1981 | Rainin | 3/13 |
| 4,328,595 | 5/1982 | Sheets | 3/13 |
| 4,340,979 | 7/1982 | Kelman | 3/13 |

*Primary Examiner*—Ronald L. Frinks
*Attorney, Agent, or Firm*—Richard L. Myers

[57] ABSTRACT

An intraocular lens for implantation within an eye after cataract surgery, etc. The intraocular lens has a free-ended, compressible, sizing prong, which sizing prong in its natural uncompressed state has a preformed closed coil spring section between its ends. This intraocular lens with its sizing prong is particularly suited for implantation within the posterior chamber behind the iris where the sizing prong is outwardly biased against the ciliary sulcus area of the eye to hold the intraocular lens in proper viewing position.

29 Claims, 4 Drawing Figures

U.S. Patent  May 8, 1984  4,446,581
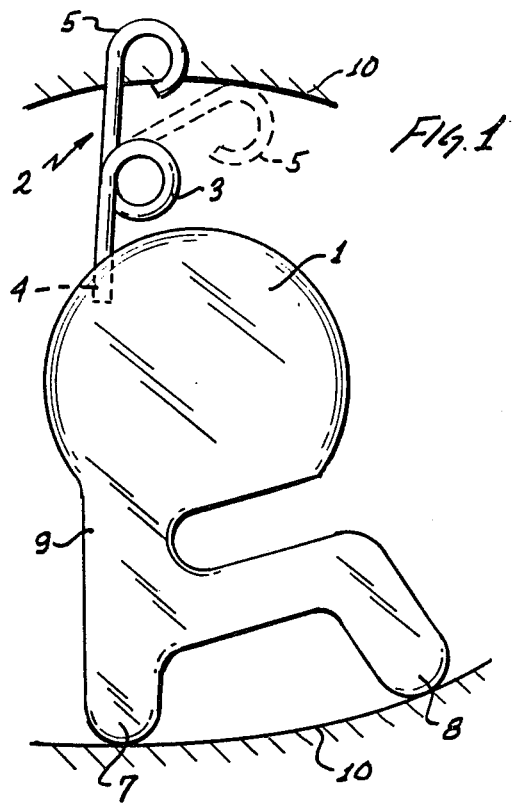
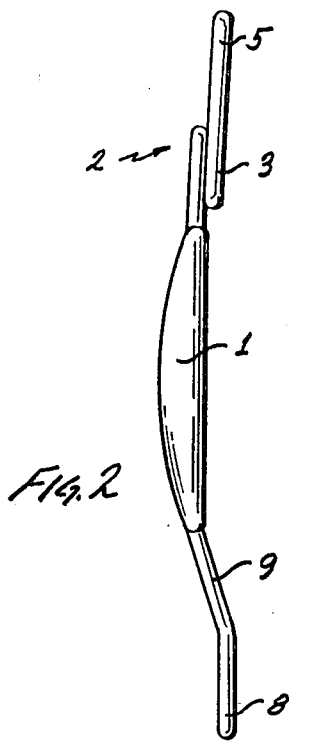
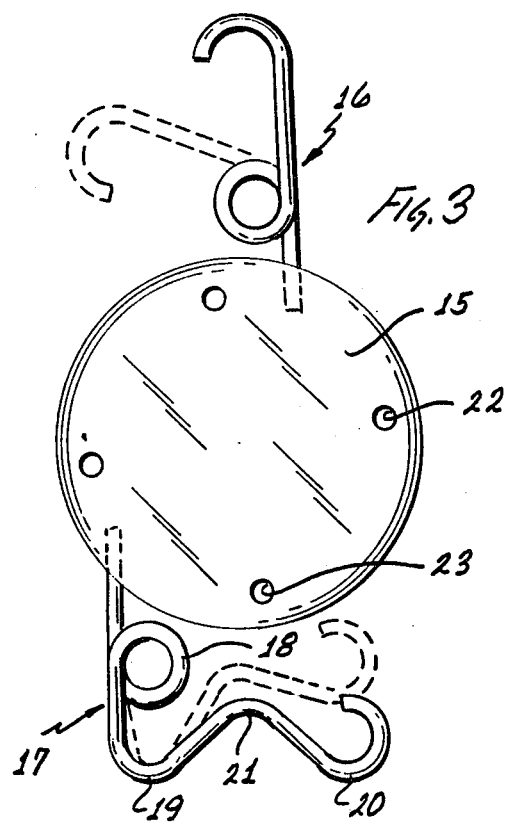
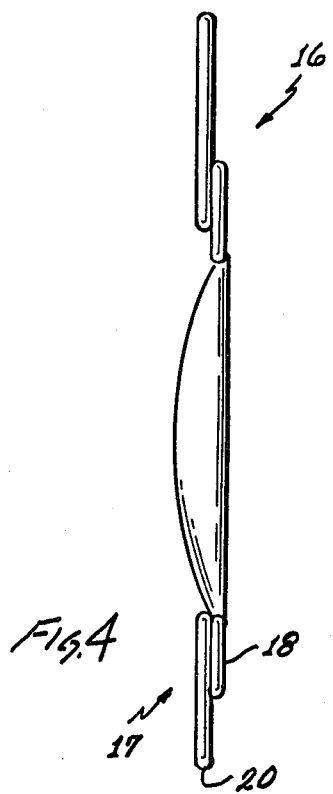

INTRAOCULAR LENS WITH FREE-ENDED SIZING PRONG

BACKGROUND

There have been many different types of intraocular lens anchoring systems for positioning the optical portion of the lens in the desired location within the eye. One type of anchoring system is described in the Richards et al U.S. Pat. Nos. 3,975,779 and 4,014,049. In these patents, an optical lens is held in position by a series of outwardly biased iris clips that are designed to expand and contract as the iris dilates and contracts.

Another type of intraocular lens positioning structure is described in the Lieb U.S. Pat. No. 2,834,023. The optical lens 20 of this patent is held in place by a pair of opposed closed loops 22 that do not connect directly to the iris. Instead, these loops 22 press outwardly against the eye's anatomy at the peripheral base of the cornea area in front of the iris. As shown in FIG. 2 of this patent, the optical lens portion 20 is in the anterior chamber of the eye.

A similar type lens in the posterior chamber is described in the Shearing U.S. Pat. No. 4,159,546. Here the optical lens 12 is held in position by a pair of J-shaped members 14 and 16 which have their outer ends curved or blunted to avoid gouging into the ciliary sulcus region of the eye directly behind the iris.

All of the above type anchoring systems for holding the optical section of the intraocular lens in position have a common problem. This problem deals with the limited flexibility of the loop or retaining structure that is outwardly urged against the eye. These eye engaging loops, prongs, etc. must be made stiff enough so as not to collapse under continual compression over the several years that the intraocular lens is likely to be within the eye. However, if the retaining structures are too stiff, excessive outward pressure against the iris (iris clip), ciliary sulcus region (posterior chamber), or peripheral base of the cornea (anterior chamber) could cause some deterioration of tissue within such area of the eye over a period of time.

SUMMARY OF THE INVENTION

The present invention overcomes the above problems by providing an intraocular lens that has a highly compressible, free-ended, sizing prong connected to the optical section of the intraocular lens. This sizing prong has a coil spring section between its ends that has a closed coil structure in the prong's natural uncompressed state prior to surgical implantation. This closed coil spring section provides substantially more "give" or flex to the prong so as to conform to the particular anatomy of the eye while holding the intraocular lens in proper position within the eye. This intraocular lens is particularly well-suited for implantation within the posterior chamber where the sizing prong gently urges outwardly against the ciliary sulcus region of the eye.

THE DRAWINGS

FIG. 1 is a front elevational view of a first embodiment of the invention;

FIG. 2 is a right end view of the lens of FIG. 1;

FIG. 3 is a front elevational view of a second embodiment of the invention; and

FIG. 4 is a right end view of the intraocular lens of FIG. 3.

DETAILED DESCRIPTION

In the first embodiment of the present invention shown in FIGS. 1 and 2, the intraocular lens has an optical lens 1 to which is secured a compressible sizing prong, shown generally at 2. The sizing prong 2 is shown in solid line in its natural uncompressed state prior to surgical implantation and in dotted line compression after implantation. This sizing prong has a closed coil loop 3 intermediate a first end 4 permanently anchored to the lens 1 and a free, unattached end 5. Preferably, a portion of the free end 5 is blunted or shaped into a generally J-shaped configuration so as not to gouge into the tissue of the eye.

When the intraocular lens is surgically implanted, the sizing prong 2 is springingly flexed about the closed coil 3 so it is gently compressed by the eye tissue. Thus, the sizing prong 2 and an additional retaining structure, such as spaced apart feet 7 and 8, on an integral extension of a haptic section 9 of the lens can firmly hold the intraouclar lens in proper position within the eye. The intraocular lens shown in FIGS. 1 and 2 is particularly suited to be surgically implanted in the posterior chamber of the eye behind the iris, such as is shown in U.S. Pat. No. 4,159,546. Thus, after capsular extraction of the natural crystalline lens, the sizing prong 2 and feet 7 and 8 of the haptic extension can engage the grooved muscular area immediately behind the iris, known as the ciliary sulcus 10. Although the ciliary sulcus would completely encircle the intraocular lens, only a portion at the top and bottom of FIG. 1 has been illustrated.

The structure of sizing prong 2, as shown in FIG. 1, provides a very high degree of "give" or flex for less chance of damaging eye tissue while firmly holding the lens in place. This is an improvement over the large, sweeping, U-shaped iris clip arms shown in FIG. 8 of U.S. Pat. No. 3,975,779 and FIG. 2 of U.S. Pat. No. 4,014,049, which have limited flexibility because they have no closed loop spring coil in their natural uncompressed state. Both of these patents have large U-shaped flexing arms with hooks for engaging the inner edge of a dilating and contracting iris. These iris engaging hooks with sharp outer ends, such as shown in FIG. 8 of U.S. Pat. No. 3,975,779, would not be practical for compressingly engaging the ciliary sulcus in a posterior chamber lens. Such sharp hook ends would gouge into and damage the eye tissue in this area.

In the second embodiment shown in FIGS. 3 and 4, an optical lens 15 has a compressible sizing prong, shown generally at 16. This prong has a configuration similar to the sizing prong of FIG. 1, but is simply reversed to show a flexing compression in dotted line toward the left. On an opposite side of lens 15 is a second retaining member in the form of a generally L-shaped sizing prong, shown at 17. Prong 17 has a preformed coil spring section 18 in its shank section that has a closed coil structure when the prong is in its natural uncompressed state prior to surgical implantation. The outer portion of prong 17 has a base portion with a pair of spaced apart protrusions 19 and 20 separated by a recess portion 21. Protrusions 19 and 20 can engage the ciliary sulcus in the same manner that the feet 7 and 8 do in the FIG. 1 embodiment. Preferably, the protrusion 20 has a blunted or curved end so as not to gouge into eye tissue. If desired, a series of suture holes, such as 22 and 23, can be provided in lens 15 for additional anchoring in the eye.

The intraocular lens described in the first and second embodiments above work very well when the optical lens is made of polymethylmethacrylate (PMMA) and the compressible sizing prong is formed of a monofilament thermoplastic material such as polypropylene. The monofilament polypropylene is of a material that is more resilient than the material (PMMA) of the lens. Preferably, the anchored end of the sizing prong is permanently secured within a pocket or other securing means on the lens.

Throughout the specification and claims, the sizing prong has been described as attached to the optical lens. It is understood that the sizing prong could be connected to any portion of the intraocular lens, such as a haptic extension of the optical lens.

In the above disclosure of the present invention, specific examples have been used to describe the invention. However, it is understood by those skilled in the art that certain modifications can be made to these examples without departing from the spirit and scope of the invention.

I claim:

1. An intraocular lens comprising: a lens; and a compressible sizing prong having one end connected to the lens and having an opposite free end; and a preformed coil spring section in the prong intermediate its ends, which coil spring section has a closed coil structure when the prong is in its natural uncompressed state prior to surgical implantation.

2. An intraocular lens as set forth in claim 1, wherein the prong has a blunted section located outwardly beyond the coil spring section, which blunted section is adapted to engage an eye.

3. An intraocular lens as set forth in claim 2, wherein the blunted section is an integral curved portion of the prong.

4. An intraocular lens as set forth in claim 3, wherein the blunted section is generally J-shaped.

5. An intraocular lens as set forth in claim 1, wherein the prong is adapted to retain the lens in an eye, and the lens has additional retaining means.

6. An intraocular lens as set forth in claim 5, wherein the additional retaining means includes an integral haptic extension of the lens.

7. An intraocular lens as set forth in claim 6, wherein the haptic extension has a pair of spaced apart feet to engage the eye.

8. An intraocular lens as set forth in claim 1, wherein there are a plurality of free ended sizing prongs connected to the lens, each sizing prong having its own coil spring section.

9. An intraocular lens as set forth in claim 8, wherein there are two sizing prongs located on opposite sides of the lens.

10. An intraocular lens as set forth in claim 1, wherein the prong and its closed coil spring section is of a single one-piece filament construction.

11. An intraocular lens as set forth in claim 1, wherein the prong, including its closed coil spring section, is of a different and more resilient material than the lens.

12. An intraocular lens as set forth in claim 11, wherein the prong, including its closed coil spring section, is of polypropylene and the lens is of polymethylmethacrylate.

13. An intraocular lens as set forth in claim 11, wherein the prong is permanently connected to the lens prior to, during, and after surgical implantation of the intraocular lens.

14. An intraocular lens as set forth in claim 1, wherein the prong has a compressible eye engaging portion extending outwardly beyond the coil spring section, whereby the eye engaging portion has a pair of spaced apart protrusions separated by a recess.

15. An intraocular lens as set forth in claim 14, wherein the prong is generally L-shaped with a shank portion connected to the lens and a base portion adapted to compressibly engage an eye.

16. An intraocular lens as set forth in claim 15, wherein the coil spring section is in the shank portion.

17. An intraocular lens as set forth in claim 15, wherein the base portion has the spaced apart protrusions with the recess therebetween.

18. An intraocular lens as set forth in claim 15, wherein an outer end segment of the base portion is inwardly curved to blunt the prong's outer end segment so as not to gouge into eye tissue.

19. An intraocular lens as set forth in claim 15, wherein there is an additional prong on the lens, and this additional prong has one end connected to the lens and has an opposite free end; said additional prong having a preformed coil spring section intermediate its ends and an eye engaging portion having a different shape from the eye engaging base portion of the other generally L-shaped prong.

20. An intraocular lens as set forth in claim 19, wherein the generally L-shaped prong has its base portion providing a pair of spaced feet separated by a recess providing a two point contact with the eye at the generally L-shaped prong; and the additional prong has a single point eye contact portion, whereby the two prongs provide a three point contact with the eye.

21. An intraocular lens comprising: a lens; a compressible sizing prong, which sizing prong has one end connected to the lens and has an opposite free end; a blunted section on the prong's free end to prevent gouging eye tissue; a preformed coil spring section in the prong between the prong's end that is connected to the lens and the prong's blunted section, which coil spring section has a closed coil structure when the prong is in its natural uncompressed state prior to surgical implantation; and an additional retaining means on the lens at a location spaced from the sizing prong.

22. An intraocular lens comprising: a lens; a compressible sizing prong, which sizing prong has one end connected to the lens and has an opposite free end; a blunt section on the prong's free end to prevent gouging eye tissue; a preformed coil section in the prong between the prong's end that is connected to the lens and the blunted section of the prong, which coil spring section has a closed coil structure when the prong is in its natural uncompressed state prior to surgical implantation; and an integral haptic extension on the lens at a location spaced from the sizing prong, said haptic extension including a pair of spaced apart protruding feet with a recess therebetween.

23. An intraocular lens comprising: a lens; a first compressible sizing prong, which first sizing prong has one end connected to the lens and has an opposite free end; a blunted section on the prong's free end to prevent gouging eye tissue; a second compressible sizing prong, which second sizing prong has one end connected to the lens and has an opposite free end; and each sizing prong has a preformed coil spring section between the prong's end connected to the lens and its blunted end, and these coil spring sections each have a closed coil structure when the prongs are in a natural uncompressed state prior to surgical implantation.

24. A posterior chamber intraocular lens comprising; a lens of a first material; a compressible sizing prong of a second material that is more resilient than the first material of the lens, which sizing prong has one end connected to the lens and has an opposite free end; a curved blunted section on the prong adapted to outwardly press against eye tissue in the posterior chamber behind the iris of an eye without substantially gouging such posterior chamber tissue; a preformed coil spring section in the prong between the prong's end connected to the lens and the curved blunted section, which coil spring section has a closed coil structure when the prong is in its natural uncompressed state prior to surgical implantation; and a posterior chamber retaining means on the lens in addition to the sizing prong.

25. A posterior chamber intraocular lens comprising: a lens of a first material; a compressible sizing prong of a second material that is more resilient than the first material of the lens, which sizing prong has one end connected to the lens and has an opposite free end; a curved blunted section on the prong adapted to outwardly press against eye tissue in the posterior chamber behind the iris of an eye without substantially gouging such posterior chamber tissue; a preformed coil spring section in the prong between the prong's end that is connected to the lens and the curved blunted section, which coil spring section has a closed coil structure when the prong is in its natural uncompressed state prior to surgical implantation; and an integral haptic extension of the lens at a location spaced from the sizing prong, said haptic extension including a pair of spaced apart protruding feet with rounded extremities and a recess therebetween, such rounded extremities of these feet adapted to outwardly press against posterior chamber eye tissue without substantial gouging of such tissue.

26. A posterior chamber intraocular lens comprising; a lens of a first material, a first compressible sizing prong of a material different from and more resilient than the first material of the lens, which first sizing prong has one end that is connected to the lens and has an opposite free end; a curved blunted section on the first prong adapted to outwardly press against eye tissue in the posterior chamber behind the iris of an eye without substantially gouging such posterior chamber tissue; a second compressible sizing prong of a different material that is more resilient than the first material of the lens, which second sizing prong has one end that is connected to the lens and has an opposite free end; a curved blunted section in the second prong adapted to outwardly press against eye tissue in the posterior chamber behind the iris of an eye without substantially gouging such posterior chamber tissue; and each sizing prong has a preformed coil spring section between the prong's end connected to the lens and its blunted end, and each coil spring section has a closed coil structure when the prongs are in a natural uncompressed state prior to surgical implantation.

27. A posterior chamber intraocular lens as set forth in claim 26, wherein the prongs have portions between their coil spring sections and their blunted sections that compressingly flex in a common circumferential direction about the lens.

28. A posterior chamber intraocular lens as set forth in claim 26, wherein one of the prongs has a pair of outwardly protruding feet separated by a recess and these feet on such prong are adapted to engage eye tissue in the posterior chamber at spaced apart locations.

29. A posterior chamber intraocular lens as set forth in claim 28, wherein such prong is generally L-shaped with a shank connected to the lens and a base adjacent the prong's free end, said coil spring section being in the shank and the protruding feet being in the base section.

* * * * *